United States Patent
Chiu et al.

(10) Patent No.: US 12,209,946 B2
(45) Date of Patent: Jan. 28, 2025

(54) SENSING METHOD OF BIOPARTICLE POSITIONING AND BIOPARTICLE POSITIONING SENSING SYSTEM

(71) Applicant: Chi-Kun Oh Yang, Taoyuan (TW)

(72) Inventors: Tzu-Keng Chiu, New Taipei (TW); Yu-Xian Zhu, Zhudong Township, Hsinchu County (TW); Chi-Kun Oh Yang, Taoyuan (TW); Cheng-Fang Yang, New Taipei (TW)

(73) Assignee: LIQBIO BIOMEDICAL COMPANY LIMITED, New Taipei (TW)

( * ) Notice: Subject to any disclaimer, the term of this patent is extended or adjusted under 35 U.S.C. 154(b) by 1051 days.

(21) Appl. No.: 17/094,212

(22) Filed: Nov. 10, 2020

(65) Prior Publication Data
US 2022/0120661 A1 Apr. 21, 2022

(30) Foreign Application Priority Data
Oct. 16, 2020 (TW) .................. 109135847

(51) Int. Cl.
*G01N 15/1434* (2024.01)
*G01N 15/14* (2006.01)
(Continued)

(52) U.S. Cl.
CPC ..... *G01N 15/1434* (2013.01); *G01N 15/1425* (2013.01); *G01N 15/1429* (2013.01);
(Continued)

(58) Field of Classification Search
CPC ........... G01N 15/1434; G01N 15/1425; G01N 15/1429; G01N 15/1443; G01N 21/6458;
(Continued)

(56) References Cited

U.S. PATENT DOCUMENTS

| 7,794,661 B2 | 9/2010 | Ikami |
| 8,879,782 B2 | 11/2014 | Hing et al. |
| 2015/0185456 A1 | 7/2015 | Kishima |

FOREIGN PATENT DOCUMENTS

CN 105051523 A 11/2015

OTHER PUBLICATIONS

Taiwanese Search Report for Taiwanese Application No. 109135847, dated Aug. 26, 2021, with an English translation.
(Continued)

*Primary Examiner* — Christopher L Chin
(74) *Attorney, Agent, or Firm* — Birch, Stewart, Kolasch & Birch, LLP

(57) ABSTRACT

A sensing method of bioparticle positioning includes the steps of: providing a carrier divided into multiple detection areas; adding bioparticle sample in the carrier, wherein the bioparticle sample includes first bioparticle with biomarker and interacts with corresponding tag; providing excitation energy that makes the tag on the first bioparticle emit radioactive energy; moving the first sensor to the detection area respectively; after receiving radioactive energy, defining the detection area where the radioactive energy comes from as activity detection area, and sending location information of the activity detection area to processing module; according to location information, moving second sensor to detection area, detecting the accurate location of the first bioparticle in activity detection area, and sending the accurate location to processing module. A bioparticle positioning sensing system is also provided herein. The method and system above detect specific bioparticle quickly and improve the detection efficiency.

16 Claims, 7 Drawing Sheets

(51) Int. Cl.
    *G01N 15/1429*     (2024.01)
    *G01N 21/64*     (2006.01)
    *G01N 33/53*     (2006.01)
    *G01N 33/543*     (2006.01)
    *G01N 33/58*     (2006.01)
    *G01N 15/10*     (2006.01)

(52) U.S. Cl.
    CPC ..... *G01N 21/6458* (2013.01); *G01N 33/5302* (2013.01); *G01N 33/54373* (2013.01); *G01N 33/582* (2013.01); *G01N 33/588* (2013.01); *G01N 2015/1006* (2013.01)

(58) Field of Classification Search
    CPC ........... G01N 21/6402; G01N 21/6428; G01N 21/645; G01N 21/6456; G01N 2021/6439; G01N 2015/144; G01N 33/5302; G01N 33/54373; G01N 33/582; G01N 33/588; G01N 2015/1006; G01B 21/008
    USPC .............. 356/311, 622, 441, 442; 422/82.05, 422/82.08, 108; 435/288.7
    See application file for complete search history.

(56) References Cited

OTHER PUBLICATIONS

Taiwanese Search Report for Taiwanese Application No. 109135847, dated May 18, 2022, with English translation.

SENSING METHOD OF BIOPARTICLE POSITIONING AND BIOPARTICLE POSITIONING SENSING SYSTEM

BACKGROUND OF THE INVENTION

1. Technical Field

The present invention relates generally to a sensing method of bioparticle positioning and a bioparticle positioning sensing system, and more particularly to a sensing method of bioparticle positioning and a bioparticle positioning sensing system, which improve the efficiency of biological particle detection.

2. Description of Related Art

With the development of science and technology, techniques of biomedical detection have also improved, wherein immunoassays improve the accuracy of detecting specific bioparticles. In the past, high-precision detection of bioparticles is mainly performed by immunofluorescence. In detail, immunofluorescence uses the immunological specificity of antibodies on fluorescent dyes and the antigens on the surface of bioparticles to target fluorescent dyes to the bioparticles. Therefore, the target bioparticles emit fluorescence under the light of a specific wavelength, which is detected by a sensor.

However, for samples with large quantities or weak fluorescence, the conventional assays cannot effectively complete the detection. For example, conventional assays use charge-coupled devices or photosensitive devices as sensors, and capture image in each visual field through the sensors; after software calculations, the images are pieced together to form a complete image, and then the specific fluorescent signal is identified by an intelligent software. The detection limit of such type of sensor is higher, so it cannot accurately detect samples with weak fluorescence, which causes a higher percentage of detection errors. In addition, such sensor takes a long time for sensing, so the detection efficiency would be low for samples with large quantities.

Therefore, a novel sensing method of bioparticle positioning and a bioparticle positioning sensing system would be needed for solving the long-standing technical problems in conventional detection methods and systems.

BRIEF SUMMARY OF THE INVENTION

In view of the above, the primary objective of the present invention is to provide a sensing method of bioparticle positioning and a system, which use a first sensor to quickly and sensitively screen and select a detection area where a specific bioparticle is located and to record location information of the detection area; next, a second sensor moves to the detection area where the specific bioparticle is located according to the location information, and performs high-precision detection to the specific bioparticle within the detection area, and then records an accurate location and related information of the specific bioparticle within an activity detection area.

The present invention provides a sensing method of bioparticle positioning, including at least the steps of:
providing a carrier and dividing the carrier into a plurality of detection areas;
adding a bioparticle sample in the carrier; the bioparticle sample includes a first bioparticle which has at least one biomarker, wherein the at least one biomarker interacts with at least one tag;
providing an excitation energy to the carrier by an excitation device, which makes the at least one tag on the first bioparticle emit a radioactive energy;
relatively moving a first sensor to the a plurality of detection areas respectively; after the first sensor receives the radioactive energy, the first sensor defines one of the detection areas where the radioactive energy comes from as an activity detection area, and further sends a location information of the activity detection area to a processing module; and
making a second sensor corresponding to the activity detection area according to the location information; detecting an accurate location of the first bioparticle in the activity detection area, and sending the accurate location to the processing module.

Another objective of the present invention is to provide a bioparticle positioning sensing system including a carrier, an excitation device, a first sensor, and a second sensor. The carrier is divided into a plurality of detection areas, wherein a bioparticle sample is provided in the carrier; the bioparticle includes a first bioparticle which has at least one biomarker; the at least one biomarker interacts with at least one tag correspondingly. The excitation device can move close to the carrier controllably and provide an excitation energy to the carrier, which makes the at least one tag on the first bioparticle emit a radioactive energy. The first sensor can move relative to the carrier controllably and move to the a plurality of detection areas respectively; after the first sensor receives the radioactive energy, the first sensor defines one of the detection areas where the radioactive energy comes from as an activity detection area, and further sends a location information of the activity detection area to a processing module. The second sensor moves to the activity detection area relative to the carrier according to the location information, wherein the second sensor detects an accurate location of the first bioparticle in the activity detection area, and sends the accurate location to the processing module.

The effect of the present invention is that, the first sensor quickly and sensitively screens and selects the detection area with the specific bioparticle, and records the location information of the detection area. Next, the second sensor moves to the detection area with the specific bioparticle according to the location information, and performs high-precision detection to the specific bioparticle within the detection area, and then records an accurate location and related information of the specific bioparticle within an activity detection area. In this way, the sensing method of bioparticle positioning and the system of the present invention provide both high detection efficiency as well as great precision so as to solve the problems encountered by conventional detection devices when detecting samples with large number or weak fluorescence.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

Figure 1:
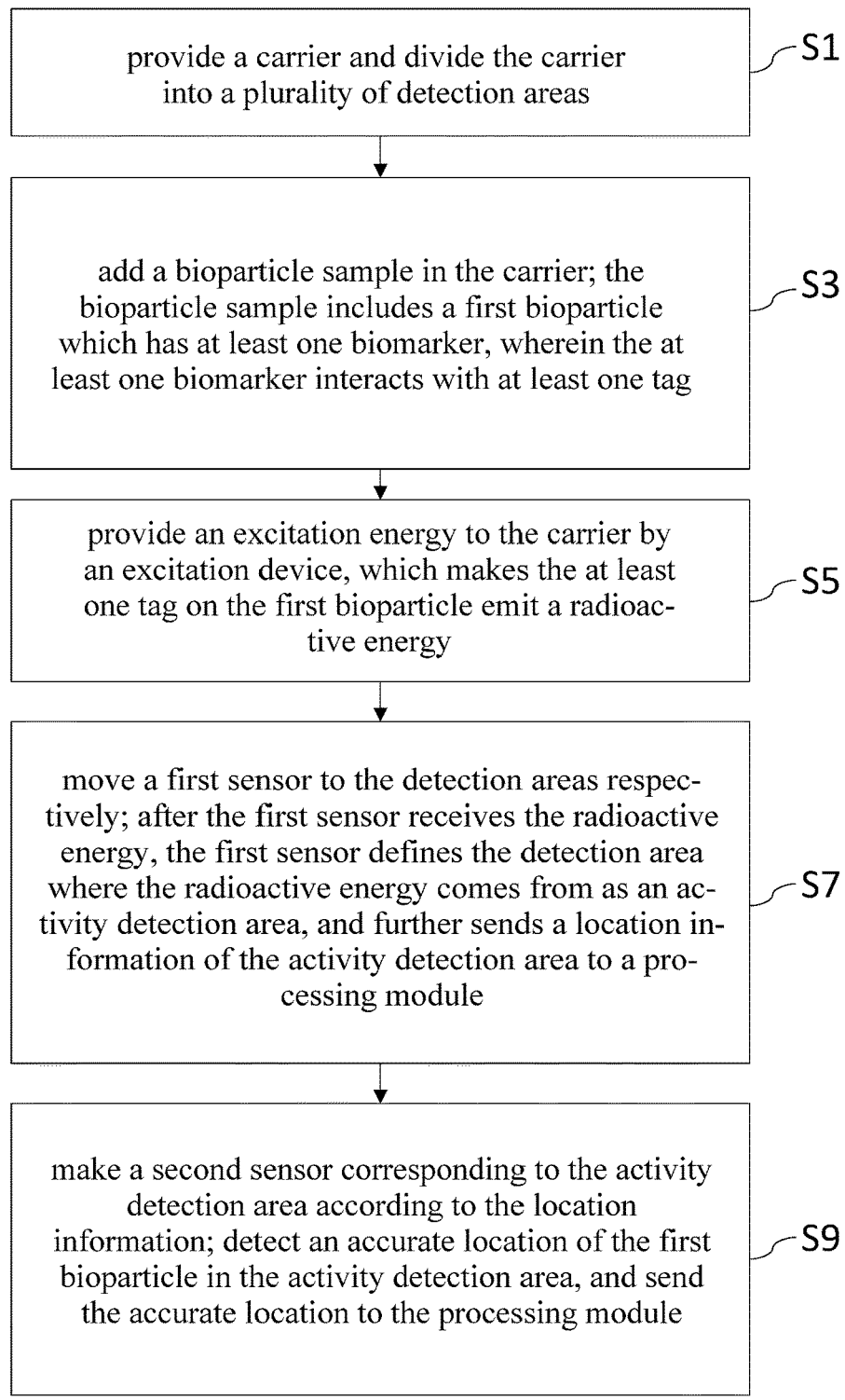
FIG. 1 is a flow chart of the sensing method of bioparticle positioning of the first embodiment of the present invention.
Figure 2:
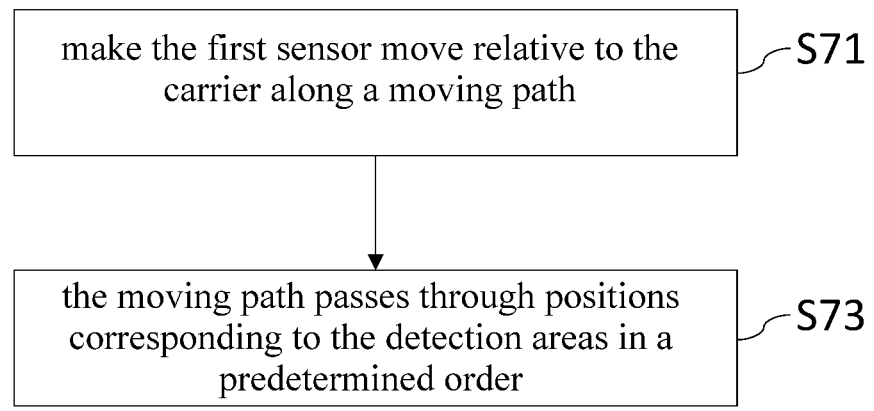
FIG. 2 is a supplementary flow chart of FIG. 1.
Figure 3:
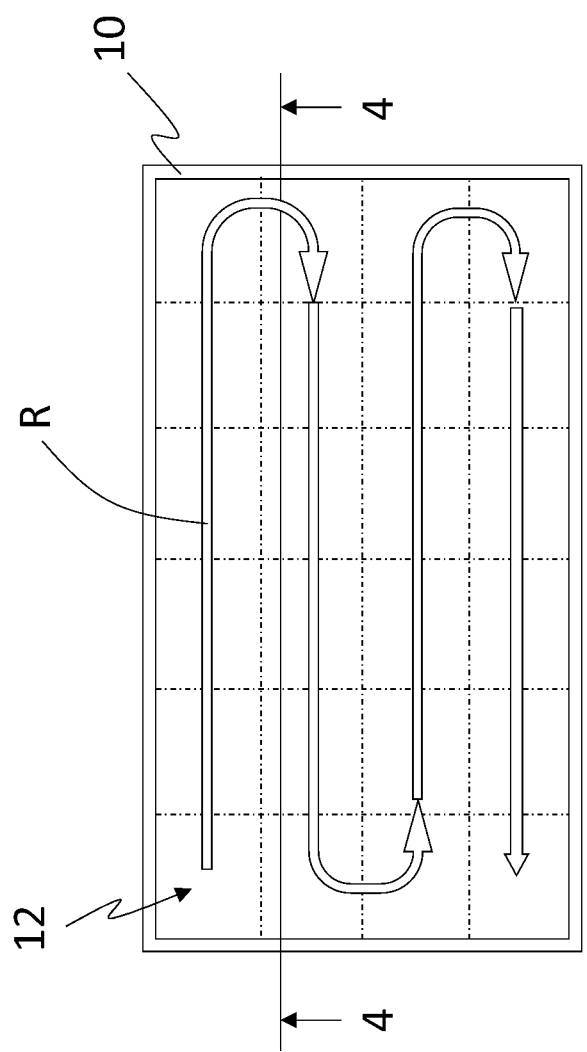
FIG. 3 is a top view of the bioparticle positioning sensing system of the first embodiment.
Figure 4:
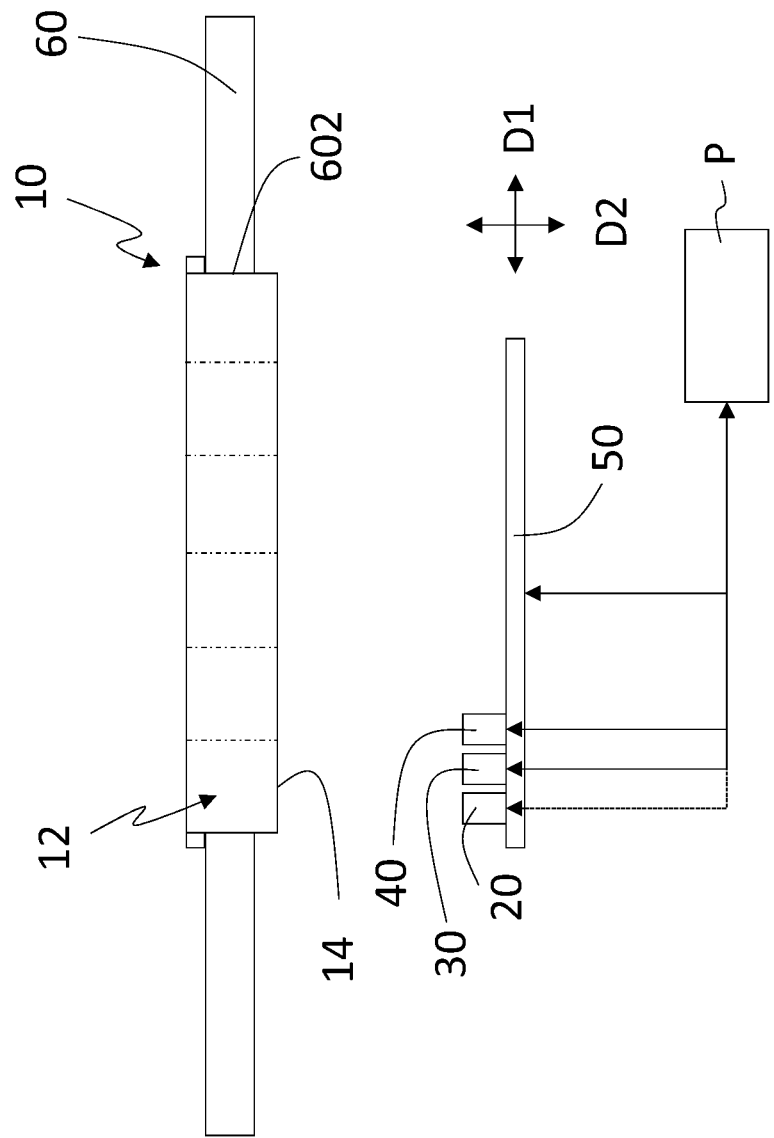
FIG. 4 is a sectional view along the 4-4 line in FIG. 3.
Figure 5:
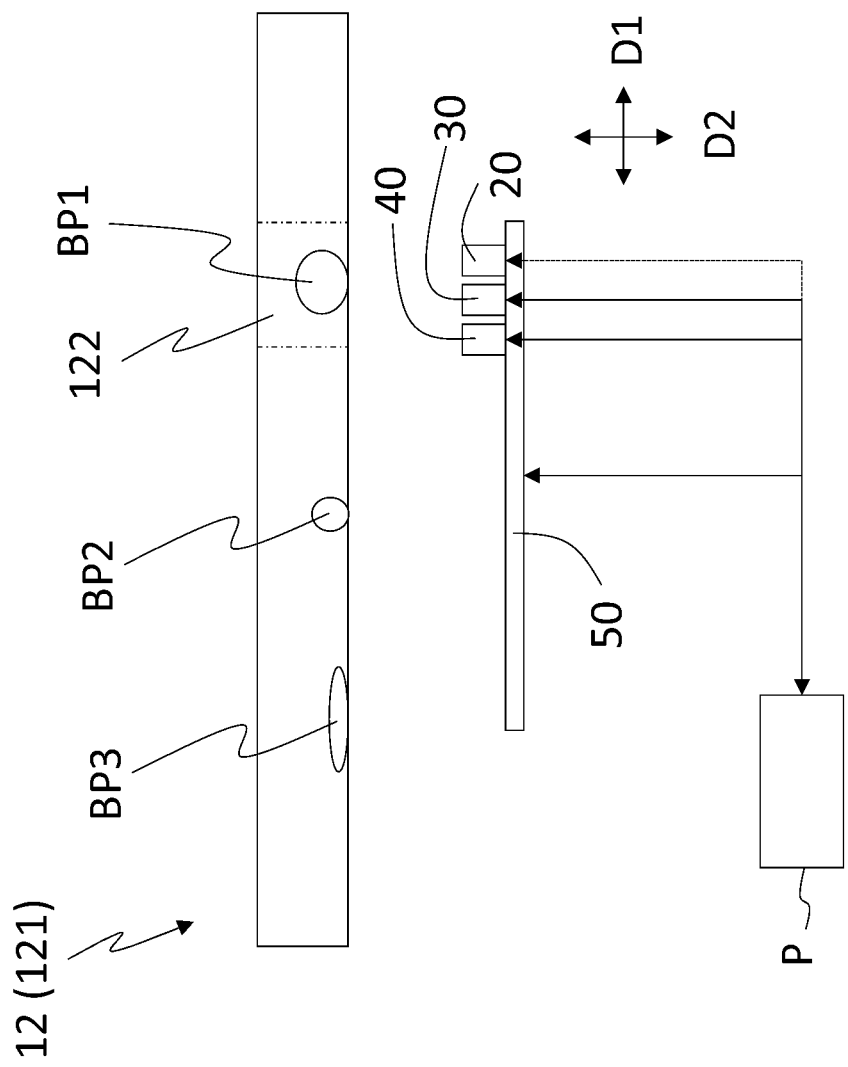
FIG. 5 is another sectional view of the bioparticle positioning sensing system of the first embodiment.
Figure 6:
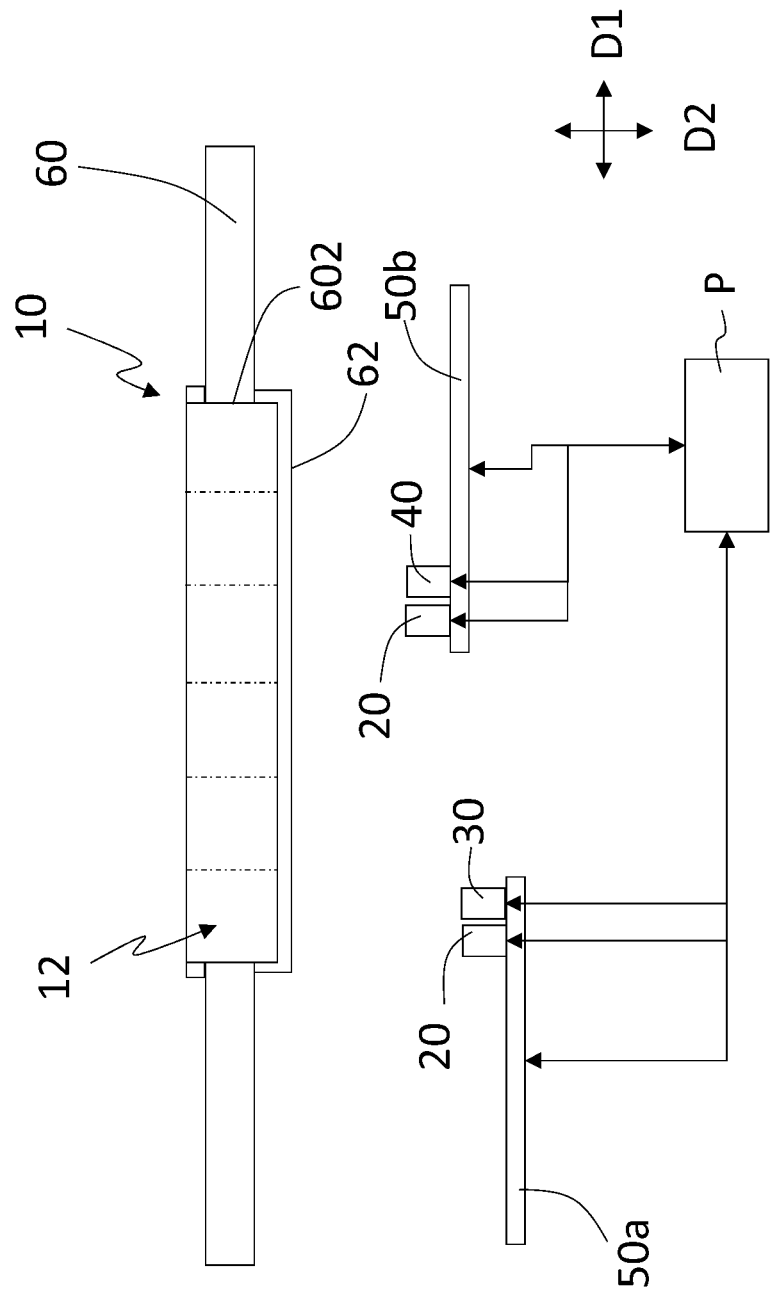
FIG. 6 is a sectional view of the bioparticle positioning sensing system of the second embodiment.

As shown in FIG. 1 to FIG. 6, FIG. 1 is a flow chart of a sensing method of bioparticle positioning of a first embodiment of the present invention; FIG. 2 is a supplementary flow chart of FIG. 1; FIG. 3 is a top view of a bioparticle positioning sensing system of the first embodiment; FIG. 4 is a sectional view along the 4-4 line in FIG. 3; FIG. 5 is another sectional view of the bioparticle positioning sensing system of the first embodiment; and FIG. 6 is a sectional view of the bioparticle positioning sensing system of a second embodiment.

As illustrated in FIG. 4 and FIG. 5, the bioparticle positioning sensing system includes a carrier 10, an excitation device 20, a first sensor 30, and a second sensor 40. The carrier 10 is divided into a plurality of detection areas 12, and a bioparticle sample BP1, BP2, BP3 is provided in the carrier 10. The bioparticle BP1, BP2, BP3 includes a first bioparticle BP1 which has at least one biomarker (not shown), wherein the at least one biomarker interacts with at least one corresponding tag (not shown).

The excitation device 20 controllably moves close to the carrier 10, and provides an excitation energy to the carrier 10, so that the at least one tag on the first bioparticle BP1 emits a radioactive energy, wherein the composition attached to the first bioparticle BP1 absorbs the excitation energy and then emits the radioactive energy. In the first embodiment, the bioparticle BP1, BP2, BP3 includes a second bioparticle BP2, BP3; the second bioparticle BP2, BP3 doesn't interact with the at least one tag, so the second bioparticle BP2, BP3 will not generate the radioactive energy. In another embodiment, the immunological binding between the at least one biomarker on the first bioparticle and the corresponding at least one tag as well as the mechanism of stimulating the fluorescent molecules on the at least one tag to emit fluorescence apply Fluorescence Resonance Energy Transfer (FRET) and Bioluminescence Resonance Energy Transfer (BRET).

The first sensor 30 controllably moves relative to the carrier 10, and moves to the detection areas 12 respectively. When the first sensor 30 moves to one of the detection areas 12, and after receiving the radioactive energy, the first sensor 30 defines the detection area 12 where the radioactive energy comes from as an activity detection area 121, and further sends a location information of the activity detection area 121 to a processing module P. The second sensor 40 moves to the activity detection area 121 according to the location information, detects an accurate location 122 of the first bioparticle BP1 in the activity detection area 121, and sends the accurate location 122 to the processing module P. In another embodiment, the carrier controllably moves relative to the first sensor so that the detection areas respectively move and corresponding to the first sensor.

As shown in FIG. 1, the sensing method of bioparticle positioning includes at least the steps below.

Step S1: provide a carrier 10, and divide the carrier 10 into a plurality of detection areas 12;

Step S3: add a bioparticle sample BP1, BP2, BP3 in the carrier 10; the bioparticle sample BP1, BP2, BP3 includes a first bioparticle BP1 which has at least one biomarker (not shown), wherein the at least one biomarker interacts with at least one tag (not shown) correspondingly;

Step S5: provide an excitation energy to the carrier 10 by an excitation device 20, which makes the at least one tag on the first bioparticle BP1 emit a radioactive energy;

Step S7: relatively move a first sensor 30 to the detection areas 12 respectively; after the first sensor 30 moves to one of the detection areas 12 correspondingly and receives the radioactive energy, the first sensor 30 defines the detection area 12 where the radioactive energy comes from as an activity detection area 121, and further sends a location information of the activity detection area 121 to a processing module P; and Step S9: make a second sensor 40 corresponding to the activity detection area 121 according to the location information, detect an accurate location 122 of the first bioparticle BP1 in the activity detection area 121, and send the accurate location 122 to the processing module P.

Based on this embodiment, in Step S3, the bioparticle BP1, BP2, BP3 includes a second bioparticle BP2, BP3 which doesn't interact with the at least one tag. Therefore, in Step S5, the second bioparticle BP2, BP3 will not generate the radioactive energy, as shown in FIG. 5. The bioparticle BP1, BP2, BP3 includes but not limited to cells, bacteria, fungi, algae, protozoa, worms, viruses, protein vectors, nucleic acid vectors, or the combinations thereof.

Based on this embodiment, the at least one biomarker includes at least one nucleic acid, protein or polysaccharide molecule on/in the bioparticle. The at least one tag includes protein, nucleic acid, polysaccharide molecule, or specific compound. In another embodiment, the at least one biomarker includes at least one surface antigen on the bioparticle. The at least one tag includes at least one antibody or chemical stain, which specifically identifies the at least one surface antigen, cytoplasmic or nuclear proteins, or nucleic acid. Furthermore, the at least one tag includes a luminescent structure, a fluorescent structure, a phosphorescent structure, a physically identifiable structure, a chemically identifiable structure, or the combination thereof. Based on the embodiment of the present invention, the at least one biomarker includes EpCAM, CD45, CD71, GPA, nucleic acid, or the combination thereof; however, it's not a limitation, and any surface antigen that may appear on the cell surface can be applied to the embodiments of the present invention. Based on the embodiment, the fluorescent structure includes fluorescent protein, Quantum Dot, or their combination. Based on this embodiment, if the at least one biomarker is EpCAM, the excitation wavelength range is 450 nm to 500 nm, and the emission wavelength range is 520 nm to 555 nm; if the at least one biomarker is nucleic acid, the excitation wavelength range is 380 nm to 420 nm, and the emission wavelength range is 540 nm to 560 nm; if the at least one biomarker is CD45, the excitation wavelength range is 600 nm to 650 nm, and the emission wavelength range is 660 nm to 720 nm. In another embodiment, compared to general fluorescent molecules, the excitation wavelength range of Quantum Dot is wider (above 10 nm), and the emission wavelength range thereof is narrow; the emission spectrum is relatively symmetrical, so every emission wavelength is far different from each other. In addition, the emission wavelength range of Quantum Dot can be adjusted by changing its particle size, so that Quantum Dots with different particle sizes can emit radiation in different emission wavelength ranges, which are excited by excitation light sources in the same excitation wavelength range. Therefore, by operating Quantum Dot materials and excitation wavelength, different types of biomarker can be targeted and identified. Furthermore, Quantum Dot has many advantages such as high fluorescence intensity, long fluorescence life, good stability, and good biocompatibility, and thus can be used to mark and recognize the biomarker on/in bioparticles.

In the first embodiment, the excitation device 20 includes a luminescence source, a laser source, a UV light source, a visible light source, an infrared source, an ultrasonic generator, an electromagnetic wave generator, a microwave generator, or the combination thereof. In Step S5, the excitation energy that is provided by the excitation device 20 to the carrier 10 includes excitation lights, excitation sound waves, excitation electromagnetic waves, or the combination thereof. Additionally, the radioactive energy emitted by the at least one tag on the first bioparticle BP1 includes optical signal, electric signal, magnetic signal, audio signal, or the combination thereof.

In this embodiment, the first sensor 30 includes a photomultiplier tube (PMT), a charge coupled device (CCD), a photoresistance, an ultrasonic sensor, an induction coil, or the combination thereof; preferably, the first sensor 30 is a photomultiplier tube (PMT) which can detect weak light sources. In this embodiment, the detection limit of the photomultiplier tube (PMT) can be less than or equal to 5V, e.g., 1V, 1.5V, 2V, 2.5V, 3V, 3.5V, 4V, 4.5V, or 5V. Preferably, the second sensor 40 is a charge coupled device (CCD) which can provide high image resolution, a complementary metal-oxide semiconductor (CMOS), or their combination, but this is not a limitation of the present invention. In the embodiment, if the radioactive energy is an optical signal, the optical signal has a first optical path to reach the first sensor, and has a second optical path to reach the second sensor, wherein the first optical path and the second optical path can be the same or different. If the first optical path and the second optical path are different, the two paths are independent optical paths.

As shown in FIG. 2 and FIG. 3, in Step S7, relatively moving the first sensor 30 to the detection areas 12 respectively includes making the first sensor 30 move relative to the carrier along a moving path R (i.e., Step S71). The moving path R passes through positions corresponding to the detection areas 12 in a predetermined order (i.e., Step S73). In the embodiment, the moving path R can be linear, so that the first sensor 30 scans line by line (as illustrated in FIG. 3); or, the moving path R can be circular so that the first sensor 30 performs circular scanning around the center of the carrier 10; or alternatively, the first sensor 30 performs other scanning methods that can pass through the detection areas. In Step S7, relatively moving the first sensor 30 to the detection areas 12 respectively means that the first sensor and the carrier move relative to each other; that is, fix the carrier and makes the first sensor controllably move relative to the carrier, or fix the first sensor and makes the carrier controllably move relative to the first sensor, which makes the detection areas respectively move to and corresponding to the first sensor.

In another embodiment, the excitation device 20, the first sensor 30, and the second sensor 40 are installed together on a mechanical arm 50. When the mechanical arm 50 moves, the excitation device 20, the first sensor 30, and the second sensor 40 move synchronously, as shown in FIG. 4 and FIG. 5. In other words, Steps S5, S7, and S9 of the sensing method of bioparticle positioning can be performed synchronously; or alternatively, Steps S5, S7, and S9 can be divided into two stages to be performed: Step S5 combined with Step S7 and Step S5 combined with Step S9. As depicted in FIG. 4 and FIG. 5, the mechanical arm 50 is controllably movable along a horizontal direction D1 and a vertical direction D2. In Step S9, the carrier can controllably move relative to the second sensor so that the activity detection areas respectively move to and are corresponding to the second sensor.

In a second embodiment, the excitation device 20 and the first sensor 30 are installed on a mechanical arm 50a, and another excitation device 20 and the second sensor 40 are installed on a mechanical arm 50b. Moreover, the excitation device 20, the first sensor 30, the second sensor 40, and the mechanical arms 50a, 50b are connected to the processing module P in signal. The excitation device 20, the first sensor 30, the second sensor 40, and the mechanical arms 50a, 50b control movement and displacement by the processing module P, as shown in FIG. 6. That is, this embodiment of the sensing method of bioparticle positioning combines Step S5 with Step S7 and combines Step S5 with Step S9 to form two performing stages. As shown in FIG. 6, the mechanical arms 50a, 50b move controllably along the horizontal direction D1 and the vertical direction D2.

As shown in FIG. 4, the carrier 10 has a transparent bottom 14, and the excitation device 20, the first sensor 30, and the second sensor 40 move under the transparent bottom 14 of the carrier 10. The carrier 10 is located in a holding groove 602 of a bearing platform 60, wherein the holding groove 602 has an opening, and the transparent bottom 14 of the carrier 10 is corresponding to the opening. Furthermore, in another embodiment, the excitation device, the first sensor, and the second sensor move above the carrier.

In this embodiment, two filter assemblies are disposed on an optical path formed between the bearing platform 60 and the first sensor 30 and an optical path formed between the bearing platform 60 and the second sensor 40 respectively. Therefore, the sensing sensitivity and accuracy of the first sensor 30 and the second sensor 40 can be improved.

For example, as shown in FIG. 6, the bearing platform 60 includes a filter assembly 62 which covers the opening. When the excitation device 20, the first sensor 30, and the second sensor 40 are moving under the carrier 10, the excitation energy and the radioactive energy are transmitted through the filter assembly 62, and thus the first sensor 30 and the second sensor 40 receive the radioactive energy. In addition, because the wavelength of excitation laser is different from the wavelength of the fluorescence released by the fluorescent molecules on the at least one tag after the fluorescent molecules are excited by the excitation laser, the filter assembly 62 on the opening at least includes a combination of lens, filter, and reflector, and thus the excitation light (i.e., laser) and emission light (i.e., fluorescence) can pass through different light paths of the filter assembly 62. Therefore, the filter assembly 62 can improve the sensing sensitivity and accuracy of the first sensor 30 and the second sensor 40.

Figure 7:
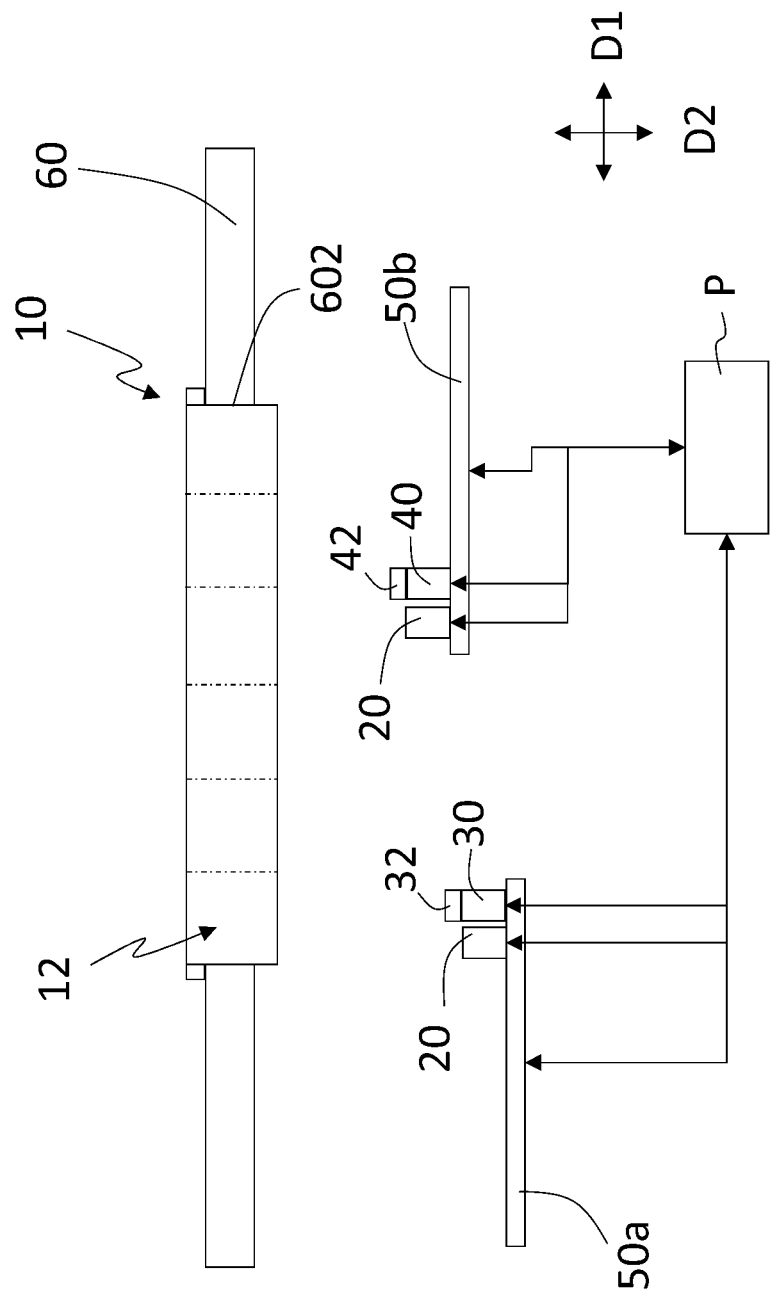
FIG. 7 is a sectional view of the bioparticle positioning sensing system of the third embodiment.

In a third embodiment as shown in FIG. 7, the first sensor 30 includes a filter assembly 32 covering a light incident surface of the first sensor 30, while the second sensor 40 includes a filter assembly 42 covering a light incident surface of the second sensor 40. When the excitation device 20, the first sensor 30, and the second sensor 40 move under the carrier 10, the excitation energy and the radioactive energy are transmitted through the filter assembly 32, 42, and thus the first sensor 30 and the second sensor 40 receive the radioactive energy. In addition, because the wavelength of excitation laser is different from the wavelength of the fluorescence released by the fluorescent molecules on the at least one tag after the fluorescent molecules are excited by the excitation laser, the filter assembly 32, 42 disposed at the opening at least includes a combination of lens, filter, and reflector, and thus the excitation light (i.e., laser) and emission light (i.e., fluorescence) can pass through different light paths of the filter assembly 32, 42. Therefore, the filter assembly 32, 42 can improve the sensing sensitivity and accuracy of the first sensor 30 and the second sensor 40.

In the preferred embodiment, the second sensor 40 is a high-speed CCD which can provide high image resolution, which is provided for identifying the accurate location 122 of the first bioparticle BP1 in the activity detection area 121 on the carrier 10, and then returning the information of the accurate location 122 in the activity detection area 121 to the processing module P. The number of the first bioparticle BP1 can be one or multiple, and the second sensor 40 can further capture the clear image of the first bioparticle BP1.

In the embodiment, the one or multiple surface antigens on the first bioparticle BP1 are bound by one or multiple antibodies, and the one or multiple antibodies are combined with one or multiple fluorescent molecules which can be excited by specific radiation sources and emit specific fluorescent signals. The photomultiplier tube (PMT) detects the fluorescent signal and initially identifies the activity detection area 121 of the first bioparticle BP1. Next, the charge coupled device (CCD) captures different fluorescent signals to identify the accurate location 122 of the first bioparticle BP1, and use the accurate location 122 to sort the first bioparticle BP1 and other bioparticle BP2, BP3.

In the embodiment, the first bioparticle BP1 can be a circulating tumor cell (CTC), and the surface antigen on the circulating tumor cell can be recognized by at least one antibody which is combined with the fluorescent molecule. For example, the EpCAM surface antigen on the circulating tumor cell (CTC) can be bound by anti-EpCAM antibodies, which generates a first fluorescent signal; anti-Hoechst antibodies can bind to the nucleic acid in the circulating tumor cell (CTC), which generates a second fluorescent signal; however, there is no CD45 antigen on the circulating tumor cell (CTC) which cannot be bound by anti-CD45 antibodies, and thus a third fluorescent signal would not be generated. Accordingly, if the photomultiplier tube (PMT) can detect the first fluorescent signal and the second fluorescent signal within a detection area but not the third fluorescent signal, it will be determined that the first bioparticle BP1, i.e., the circulating tumor cell (CTC), located in the detection area; then, the photomultiplier tube (PMT) returns the location of the circulating tumor cell (CTC) in the detection area 12 to the processing module P.

In another embodiment, if the photomultiplier tube (PMT) cannot detect the first fluorescent signal or second fluorescent signal in a detection area where the second bioparticle BP2 is located, or if photomultiplier tube (PMT) detects the third fluorescent signal, it will be determined that the second bioparticle BP2 is not circulating tumor cell (CTC), that is, the first bioparticle BP1 is not located in the detection area. In this time, the photomultiplier tube (PMT) will skip the detection area where the second bioparticle BP2 is located. Alternatively, if the photomultiplier tube (PMT) detects only one of the first fluorescent signal and the second fluorescent signal in a detection area where the third bioparticle BP3 is located, it will be determined that the third bioparticle BP3 is not circulating tumor cell (CTC). In this time, the photomultiplier tube (PMT) will skip the detection area where the third bioparticle BP3 is located. In this embodiment, the photomultiplier tube (PMT) quickly scans and detects the fluorescent signals in the detection areas where the bioparticles BP1, BP2, BP3 may be located, and immediately determines whether the bioparticles BP1, BP2, BP3 are located in the detection areas, and further records the location of the first bioparticle BP1 in the activity detection area 121 immediately.

Next, after the photomultiplier tube (PMT) returns the location of the circulating tumor cell (CTC) in the activity detection area 121 to the processing module P as well as excludes detection areas where circulating tumor cell (CTC) is not located, the charge coupled device (CCD) moves to the activity detection area 121. If the charge coupled device (CCD) detects the bioparticle which emits the first fluorescent signal and the second fluorescent signal but not the third fluorescent signal under the visual field of the detection area 12, it will be determined that the detected first bioparticle BP1 is circulating tumor cell (CTC). Afterward, the charge coupled device (CCD) returns the accurate location 122 of the circulating tumor cell (CTC) in the activity detection area 121 to the processing module P, and then the first bioparticle BP1 will be recognized by the accurate location 122 sent by the charge coupled device (CCD).

Based on the embodiment of the present invention, the first sensor quickly and sensitively screens and selects the detection area where the specific bioparticle is located, and records the location information of the detection area. Next, the second sensor moves to the detection area where the specific bioparticle is located according to the location information, and performs high-precision detection to the specific bioparticle within the detection area, and then records the accurate location and related information of the specific bioparticle within the activity detection area. In this way, the sensing method of bioparticle positioning and the system of the present invention provide both high detection efficiency as well as great precision so as to solve the problems encountered by conventional detection devices when detecting samples with large number or weak fluorescence.

The embodiments described above are only preferred embodiments of the present invention. All equivalent structures and methods which employ the concepts disclosed in this specification and the appended claims should fall within the scope of the present invention.

What is claimed is:

1. A bioparticle positioning sensing system, comprising:
a carrier which is divided into a plurality of detection areas, wherein a bioparticle sample is provided in the carrier; the bioparticle comprises a first bioparticle which has at least one biomarker; the at least one biomarker interacts with at least one tag correspondingly;
an excitation device which can move close to the carrier controllably and provide an excitation energy to the carrier, which makes the at least one tag on the first bioparticle emit a radioactive energy;
a first sensor which can move relative to the carrier controllably and move to the plurality of detection areas respectively; after the first sensor receives the radioactive energy, the first sensor defines one of the detection areas where the radioactive energy comes from as an activity detection area, and further sends a location information of the activity detection area to a processing module; and
a second sensor which moves to the activity detection area relative to the carrier according to the location information, wherein the second sensor detects a location of the first bioparticle in the activity detection area, and sends the location to the processing module.

2. The bioparticle positioning sensing system of claim 1, wherein the bioparticle comprises a second bioparticle which does not interact with the at least one tag.

3. The bioparticle positioning sensing system of claim 1, wherein moving the first sensor to the detection areas respectively comprises the step of:
making the first sensor move relative to the carrier along a moving path, wherein the moving path passes through positions corresponding to the detection areas in a predetermined order.

4. The bioparticle positioning sensing system of claim 1, wherein the bioparticle comprises a cell, bacteria, fungi, algae, protozoa, worms, virus, protein vector, nucleic acid vector, or a combination thereof.

5. The bioparticle positioning sensing system of claim 1, wherein the at least one biomarker comprises at least one surface antigen on the first bioparticle; the at least one tag comprises at least one antibody for specifically identifying the at least one surface antigen.

6. The bioparticle positioning sensing system of claim 1, wherein the at least one tag comprises a luminescent structure, a fluorescent structure, a phosphorescent structure, or a combination thereof.

7. The bioparticle positioning sensing system of claim 6, wherein the fluorescent structure comprises fluorescent protein, Quantum Dot, or their combination.

8. The bioparticle positioning sensing system of claim 6, wherein the excitation device comprises a luminescence source, a laser source, a UV light source, a visible light source, an infrared source, an ultrasonic generator, an electromagnetic wave generator, a microwave generator, or a combination thereof.

9. The bioparticle positioning sensing system of claim 8, wherein the radioactive energy comprises optical signal, electric signal, magnetic signal, audio signal, or a combination thereof.

10. The bioparticle positioning sensing system of claim 9, wherein the first sensor comprises a photomultiplier tube (PMT), a charge coupled device (CCD), a photoresistor, an ultrasonic sensor, an induction coil, or a combination thereof.

11. The bioparticle positioning sensing system of claim 9, wherein the second sensor comprises a charge coupled device (CCD), a complementary metal-oxide semiconductor (CMOS), or their combination.

12. The bioparticle positioning sensing system of claim 9, wherein if the radioactive energy is the optical signal, the optical signal has a first optical path to reach the first sensor, and has a second optical path to reach the second sensor; the first optical path and the second optical path can be the same or different.

13. The bioparticle positioning sensing system of claim 1, wherein the excitation device, the first sensor, and the second sensor are installed together on a mechanical arm; when the mechanical arm moves, the excitation device, the first sensor, and the second sensor move synchronously.

14. The bioparticle positioning sensing system of claim 1, wherein the excitation device and the first sensor are installed on a mechanical arm, while another excitation device and the second sensor are installed on another mechanical arm; the excitation devices, the first sensor, the second sensor, and the mechanical arms are connected to the processing module in signal; the excitation devices, the first sensor, the second sensor, and the mechanical arms control movement and displacement by the processing module.

15. The bioparticle positioning sensing system of claim 1, wherein the carrier has a transparent bottom; the excitation device, the first sensor, and the second sensor move under the transparent bottom of the carrier.

16. The bioparticle positioning sensing system of claim 15, wherein the carrier is provided in a holding groove of a bearing platform; the holding groove has an opening, and the transparent bottom of the carrier is corresponding to the opening; the bearing platform comprises a filter assembly which covers the opening; when the excitation device, the first sensor, and the second sensor are moving under the carrier, the excitation energy and the radioactive energy are transmitted through the filter assembly, which makes the first sensor and the second sensor receive the radioactive energy.

* * * * *